United States Patent
Montagu et al.

(10) Patent No.: US 6,586,750 B2
(45) Date of Patent: Jul. 1, 2003

(54) HIGH PERFORMANCE SUBSTRATE SCANNING

(75) Inventors: Jean I. Montagu, Brookline, MA (US); David Stern, Mountain View, CA (US)

(73) Assignee: Perlegen Sciences, Mountain View, CA (US)

( * ) Notice: Subject to any disclaimer, the term of this patent is extended or adjusted under 35 U.S.C. 154(b) by 12 days.

(21) Appl. No.: 09/922,492

(22) Filed: Aug. 3, 2001

(65) Prior Publication Data

US 2002/0074512 A1 Jun. 20, 2002

Related U.S. Application Data

(60) Provisional application No. 60/223,278, filed on Aug. 3, 2000.

(51) Int. Cl.[7] ............................................... G01N 21/64
(52) U.S. Cl. ................... 250/458.1; 250/459.1
(58) Field of Search .......................... 250/458.1, 459.1, 250/461.1; 422/82.08; 356/317, 318; 436/63, 172

(56) References Cited

U.S. PATENT DOCUMENTS

| | | | |
|---|---|---|---|
| 5,224,088 A | 6/1993 | Atiya | 369/97 |
| 5,459,325 A | 10/1995 | Hueton et al. | 250/458.1 |
| 5,578,832 A | 11/1996 | Trulson et al. | 250/458.1 |
| 5,631,734 A | 5/1997 | Stern et al. | 356/317 |
| 5,834,758 A | 11/1998 | Trulson et al. | 250/201.2 |
| 5,981,956 A | 11/1999 | Stern | 250/458.1 |
| 6,025,601 A | 2/2000 | Trulson et al. | 250/461.2 |
| 6,141,096 A | 10/2000 | Stern et al. | 356/318 |
| 6,201,639 B1 * | 3/2001 | Overbeck | 359/368 |
| 6,207,960 B1 | 3/2001 | Stern | 250/458.1 |
| 6,225,625 B1 | 5/2001 | Pirrung et al. | 250/302 |
| 6,248,988 B1 | 6/2001 | Krantz | 250/201.3 |
| 6,252,236 B1 | 6/2001 | Trulson et al. | 250/458.1 |
| 6,262,838 B1 | 7/2001 | Montagu | 359/392 |

FOREIGN PATENT DOCUMENTS

| | | | | |
|---|---|---|---|---|
| EP | 0 729 265 A | 8/1996 | | H04N/1/192 |
| WO | 98 38495 A | 9/1998 | | G01N/21/64 |
| WO | 99 47964 A | 9/1999 | | G02B/26/08 |

OTHER PUBLICATIONS

International Search Report, International application No. PCT/US 01/24440, Date of mailing Jan 28, 2003.

* cited by examiner

*Primary Examiner*—Constantine Hannaher
*Assistant Examiner*—Timothy Moran
(74) *Attorney, Agent, or Firm*—Moser, Patterson & Sheridan, L.L.P.

(57) ABSTRACT

An optical scanning system for examining material associated with a substrate includes at least one scanning module for displacing two or more objective lenses, at least one optical coupling system and a translation system. The two objective lenses are mounted on one or more scan arms and are constructed to scan over regions or subregions associated with the substrate. The scanning module is configured to displace the scan arm(s) to perform the scan and thereby displace the two objective lenses. Each objective lens is arranged to deliver light to the material and collect light from the material.

38 Claims, 7 Drawing Sheets

HIGH PERFORMANCE SUBSTRATE SCANNING

CROSS-REFERENCE TO RELATED APPLICATIONS

This application claims priority from U.S. Provisional Application 60/223,278, filed on Aug. 3, 2000, entitled "High Performance Wafer Scanning" which is incorporated herein by reference in its entirety.

BACKGROUND OF THE INVENTION

1. Field of the Invention

The present invention relates to optical scanning systems for examining material disposed on a substrate.

2. Description of the Related Art

Microarray technology has been used to analyze a large number of complex biochemical reactions and systems in parallel. Optical scanners examine microarrays using a light beam having a few micron spot size. This technology provides a massively parallel form of analysis that increases data collection per unit time, decreases the overall time required for analysis, and uses smaller sample volumes and reagent volumes. For these and other reasons, microarray technology is well suited for genomic research.

Microarrays with an extremely large number of features are manufactured by methods described in PCT Application WO 92/10092 or U.S. Pat. Nos. 5,143,854; 5,384,261; 5,405,783; 5,412,087; 5,424,186; 5,445,934; 5,744,305; 5,800,992; 6,040,138; 6,040,193 all of which are incorporated by reference. The array features usually have dimensions from about ten (10) microns to about one hundred (100) microns. Each feature can include several million DNA molecules. The synthesis area of a substrate may be about 110 mm×110 mm and may include several individual microarray chips. An optical scanner needs to scan approximately 65,536×65,536 pixels, for microarrays having feature sizes of 10 µm to 12.5 µm, and approximately 32,768×32,768 pixels, for microarrays having feature sizes of 20 µm to 25 µm. Depending on the scanner, such scans take from several hours to several days.

The above-mentioned microarrays can be scanned by various optical scanners such as confocal galvanometer scanners described in U.S. Pat. No. 5,981,956 (which is incorporated by reference) or flying objective scanners described in U.S. Pat. No. 5,459,325 or PCT Applications PCT U599/06097 or PCT U599/24049 (all of which are incorporated by reference.). However, a reliable scanner that performs scans in a smaller amount of time would be useful in the art.

There is a need for additional high-speed, high-resolution optical scanning systems constructed and arranged for examination of biological material disposed on a substrate.

SUMMARY OF THE INVENTION

The present invention is directed to scanning systems and methods for examination of biological material associated with a substrate.

Thus, one aspect of the present invention provides an optical scanner, comprising: at least a first and a second objective lens mounted on at least one scanning module, wherein each at least one scanning module comprises at least one motor, at least one scan arm and at least one of the objective lenses; an optical coupling system comprising a light source and at least a first and second detector, wherein said optical coupling system is configured to deliver light from said light source through said at least two objective lenses to a substrate and detect light from said substrate collected by said at least a first and a second objective lens, and wherein said first detector detects light from said first objective lens and said second detector detects light from said second objective lens and so on; and a translation mechanism constructed for relative movement of said substrate and said scanning module. One such embodiment of this aspect of the invention provides an optical scanner, comprising: a first and a second scanning module, wherein each of said scanning modules comprises a motor, a scan arm and an objective lens; an optical coupling system comprising a light source and a first and a second detector, wherein said optical coupling system is configured to deliver light from said light source through said first and second objective lenses to a substrate and detect light from said substrate collected by said first and second objective lenses, and wherein said first detector detects light from said first objective lens and said second detector detects light from said second objective lens; and a translation mechanism constructed for relative movement of said substrate and said scanning module.

Another aspect of the present invention provides an optical scanning method for examining biological material, comprising the steps of: providing two objective lenses mounted on at least one scanning module, wherein each of said at least one scanning module comprises at least one motor, at least one scan arm and at least one of the at least one objective lenses; generating light of a selected wavelength and coupling said generated light to said two objective lenses; displacing said at least one scanning module on a scan path over biological material disposed on regions of a substrate; irradiating said biological material by light from each objective lens; collecting light from said biological material by each objective lens; detecting by a separate detector light collected from each objective lens; and analyzing said biological material based on said light detected by said detectors.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
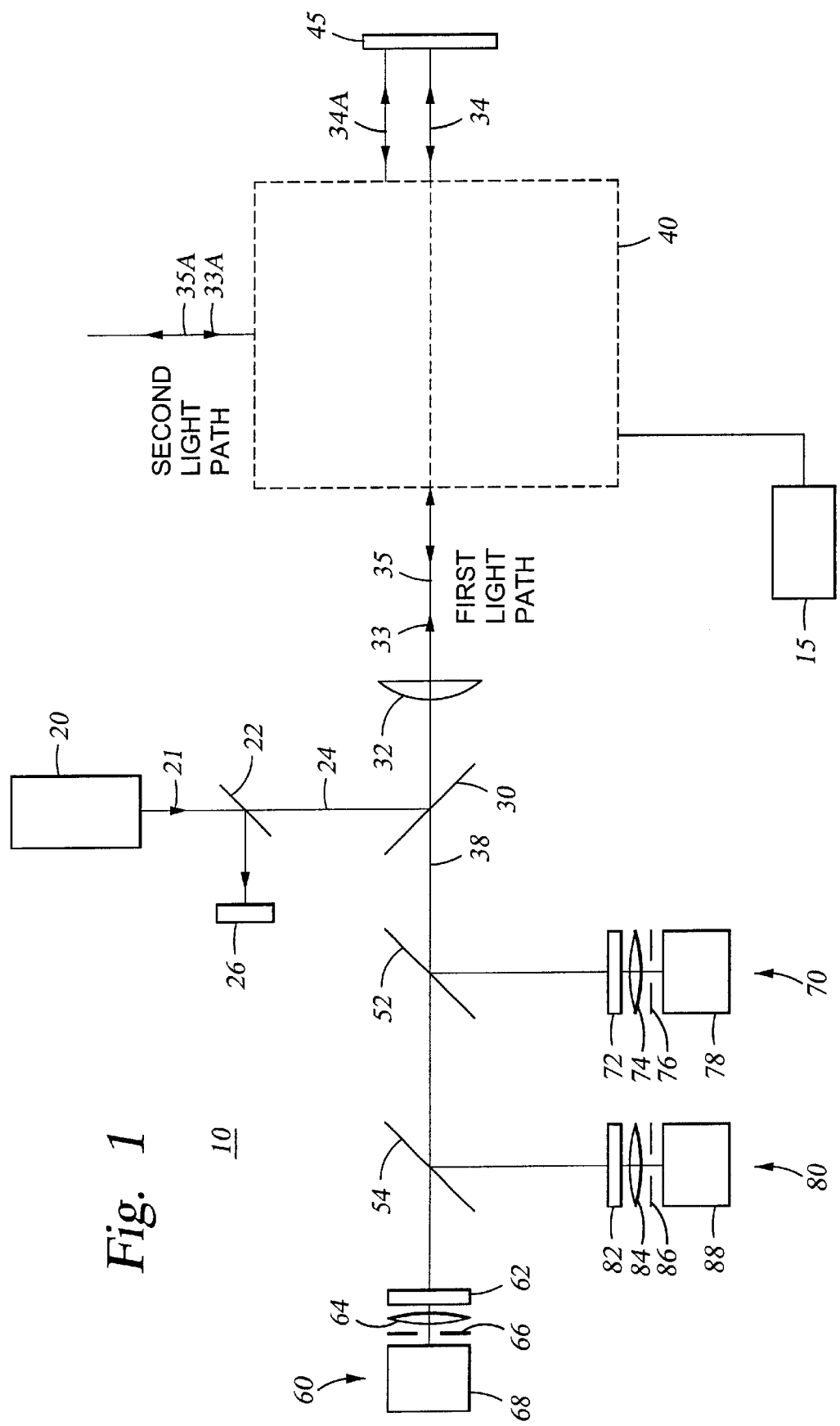
FIG. 1 is a schematic illustration of an optical scanning system for examining large area substrates.
Figure 2:
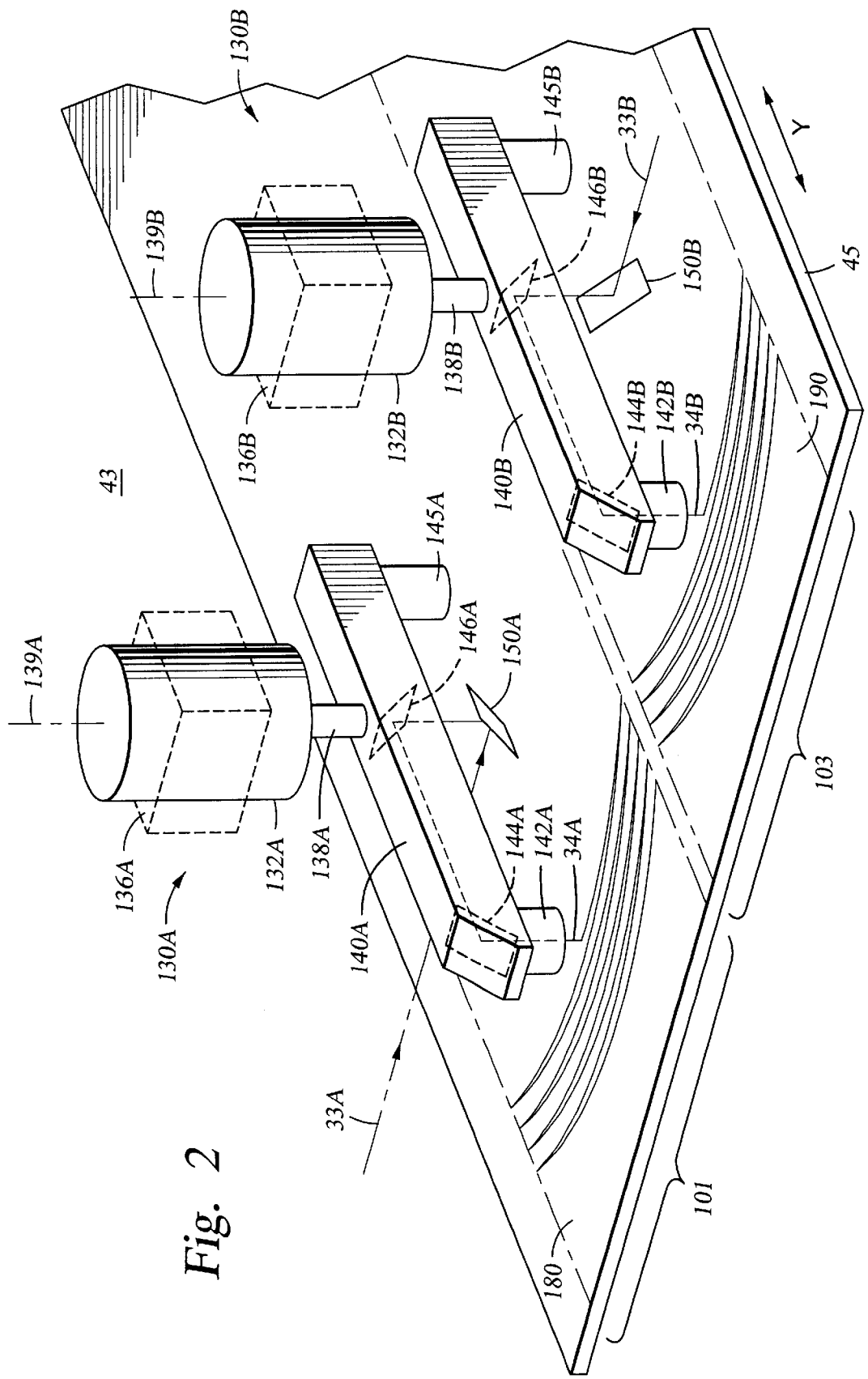
FIG. 2 is a perspective view of an arc scanning system with two scanning modules each carrying a flying objective lens.
Figure 3:
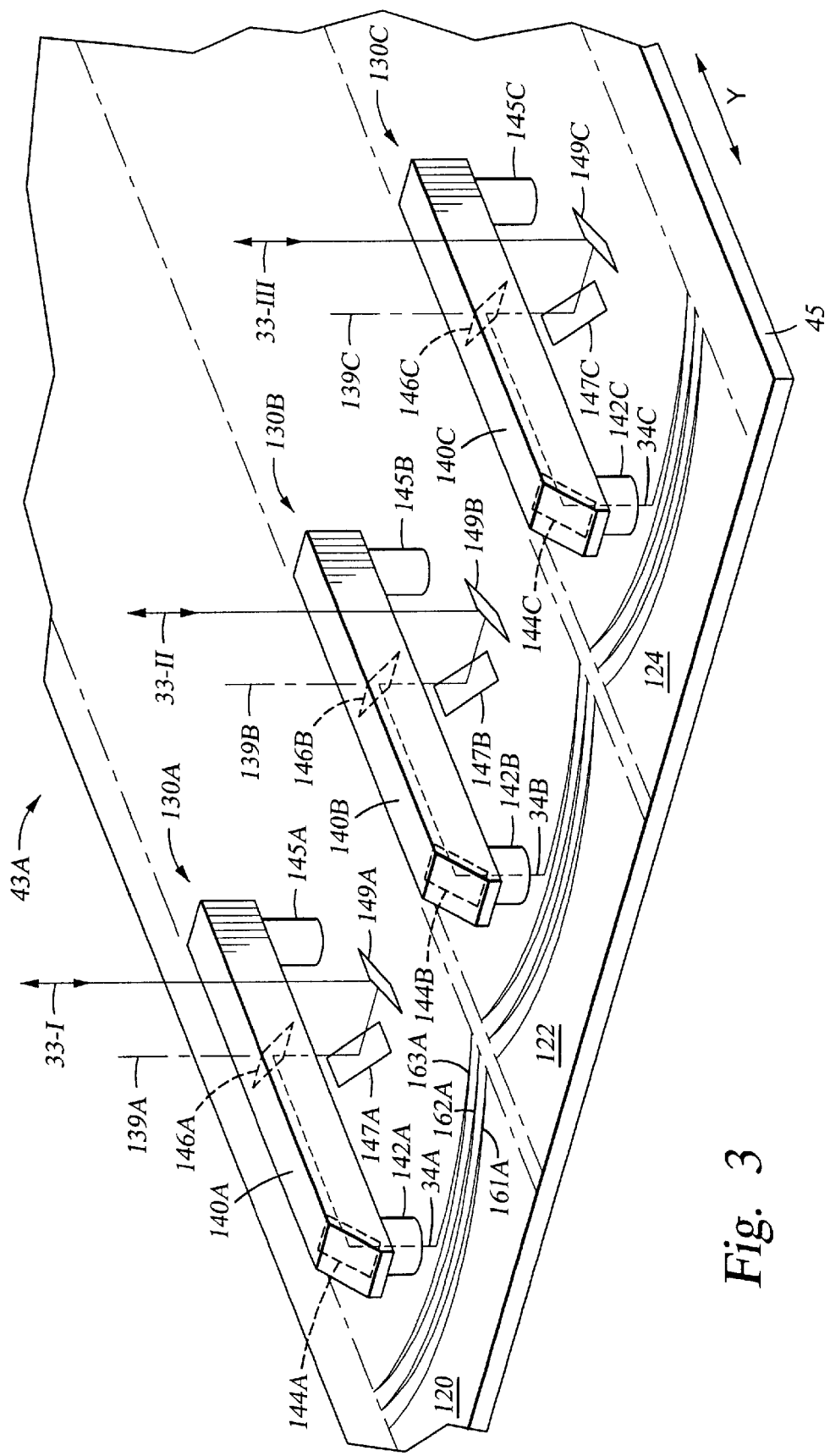
FIG. 3 is a perspective view of another arc scanning system with three scanning modules each carrying a flying objective lens.
Figure 4:
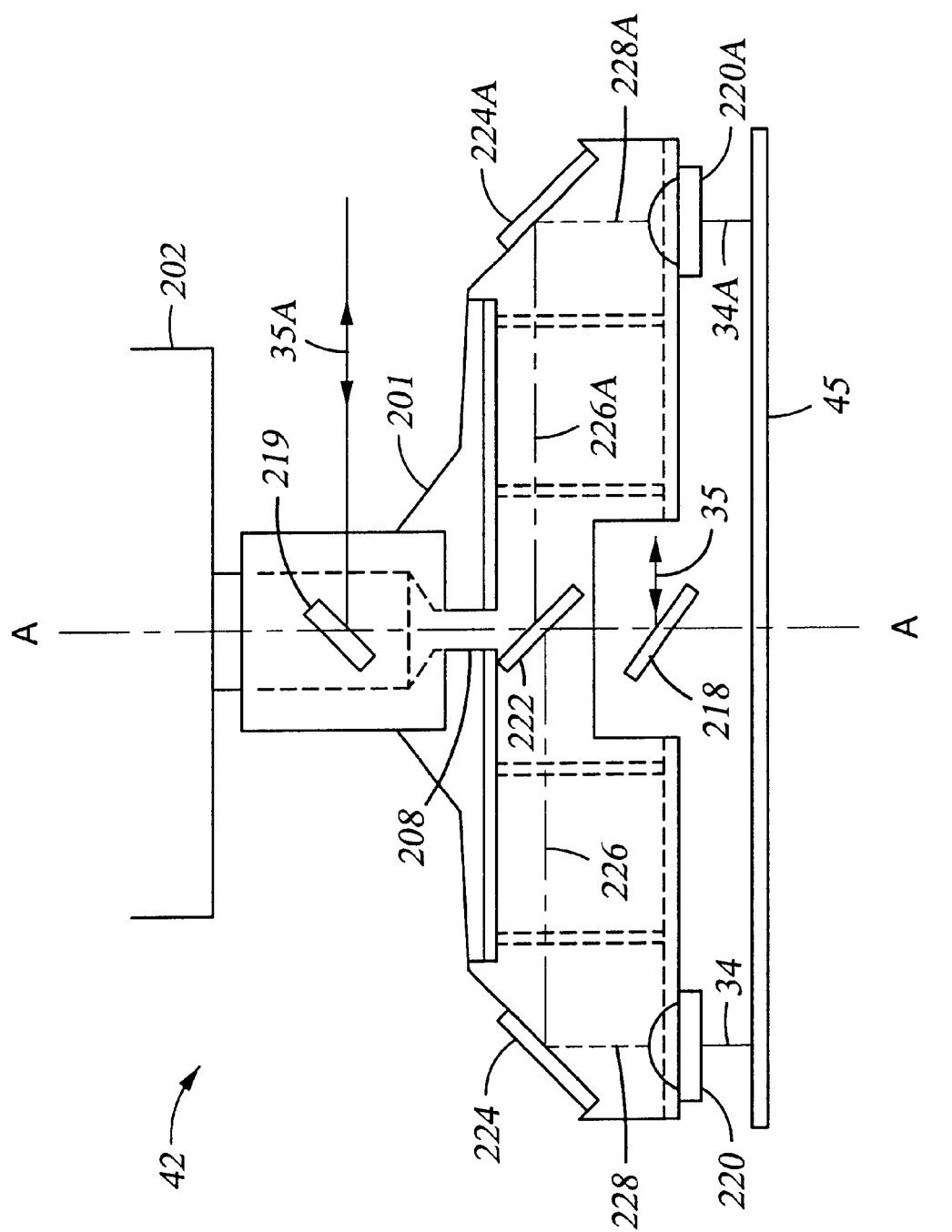
FIG. 4 is a side view of a single scanning module carrying two flying objective lenses.

FIG. 1 schematically illustrates an optical scanning system 10, which includes an optical coupling system comprising at least one light source, at least two optical detectors, alight path, a scanning module and a controller. The optical coupling system may include dichroic beamsplitters, spectral filters, lenses, pinholes and several channels for detecting wavelength specific radiation. The scanning module may have either a rectilinear flying objective design or a rotating (arc) flying objective design (as shown in FIGS. 2–4). Both types of scanning modules (i.e., the rectilinear or arc flying objective design) are constructed to deliver at least two focused light beams (i.e., examination beams) to a surface of a large area substrate.

To deliver the light beams, the optical scanning system uses at least two objective lenses. Each objective lens of the rectilinear flying objective design moves over a first dimension (e.g., substantially X axis) of a substrate to focus light onto the surface of the substrate. A translation table displaces the substrate in a second dimension (e.g., substantially Y axis) that is usually perpendicular to the first dimension. Alternatively, the arc design moves the objective lenses over essentially a first dimension of the array, and the translation table displaces the substrate over a second dimension (e.g., Y axis). In one embodiment, the optical scanning system is used to obtain images of oligonucleotide microarrays to which fluorescently labeled DNAs or RNAs are bound, images of polypeptide or other polymer arrays, electrophoresis gels, or other biological material.

The term "pixel size" as used herein means the center-to-center displacement of a laser beam between adjacent sample points. Each sample point is associated with a respective analog-to-digital (AID) conversion of the photodetector output.

FIG. 1 is a block diagram of an optical scanning system. The optical scanning system of FIG. 1 comprises a controller 15, an optical source 20, a mechanical scanning system or translator 40, a plurality of optical detection channels 60, 70 and 80, and various optical processing devices. The optical scanning system operates to generate a plurality of light beams, couple the generated light beams to various portions of a substrate 45 using the mechanical scanning apparatus 40, and detect fluorescence from various positions on the substrate 45.

The optical source 20 may comprise a laser such as an argon laser, diode laser, helium-neon laser, dye laser, titanium sapphire laser or Neodinium YAG laser. The selected wavelength of the light produced by laser 20 depends upon the composition of substrate 45. For example, the wavelength of light may be selected to be of a wavelength absorbed by fluorophores on the substrate 45 such that the fluorophores disposed thereon are able to fluoresce. In one embodiment, the selected wavelength of light produced by laser 20 is within the visible spectrum. However, ultraviolet (UV), near infrared (NIR) or infrared (IR) wavelengths may also be used to practice the present invention.

The laser 20 emits a light beam 21 which is communicated to the mechanical scanning apparatus 40 via a dichroic beam splitter 30. One or more mirrors, lenses or prisms can be optionally interposed between the dichroic beam splitter 30 and the mechanical scanning system 40 to ensure that a laser light beam having an appropriate diameter is delivered to the objective lens. In one embodiment, the light beam 21 is partially reflected or diverted by a beam splitter 22 to an optical power measuring device 26, such as a photodetector.

The light 21 produced by the laser 20 is communicated by a path 24 to the dichroic beam splitter 30. A first light path 33 communicates the reflected light from the dichroic beam splitter 30 to the mechanical scanning system 40. The first light path has a forward path 33 and a reverse path 35 where the forward path 33 provides light to the mechanical scanning apparatus 40 and the reverse path 35 receives light from the mechanical scanning apparatus 40.

The mechanical scanning system 40 causes light received by the first light path 33 to be imparted to the substrate 45 according to a predefined scanning pattern. That is, mechanical scanning system 40 delivers at least one focused beam of light 34 to a series of positions on the substrate 45. Light that is emitted, reflected, or otherwise returned from each scanned position on the substrate 45 and received by the mechanical scanning apparatus 40 and transmitted back to the dichroic splitter 30 via a return path 35 of the first light path.

The dichroic splitter 30 separates light of differing wavelengths collected from the substrate and passed through mechanical scanning device 40. Typically, the dichroic beam splitter reflects light having shorter wavelengths and transmits light having longer wavelengths. The selected light wavelength of interest is then passed to a second splitter. The second splitter 52 diverts a first portion of its received light to a first optical channel 70, and a remaining portion of the received light to a third splitter 54. The third splitter 54 diverts a first portion of its received light to a second optical channel 80 and a remaining portion of its received light to a third optical channel 60.

Each of the optical channels 60, 70 and 80 operate in substantially the same way and will be described simultaneously. Specifically, each optical channel 60, 70 and 80 comprises a respective filter 62, 72 and 82 adapted to pass light having a predefined wavelength or wavelength range. The light passed by the respective filters 62, 72 and 82 is received by respective focusing elements or lenses 64, 74, 82, which lenses focus their respective received light beams onto pinhole elements 66, 76 and 86. Light that is transmitted through the pinhole elements is then passed on to respective photodetectors (68, 78 and 88). In this respect, the optical system functions as a confocal microscope. In an alternative embodiment, the pinhole elements can be eliminated from the structure and the light can be focused onto the respective photodetectors.

Each of the optical channels 60, 70 and 80 may operate on different wavelengths of light or similar wavelengths of light. Each of the filters 62, 72 and 82 may pass light having the same wavelength or different wavelengths. In one embodiment, one optical channel operates on light having a wavelength between substantially 515 nm and 545 nm, a second optical channel operates on light having a wavelength between substantially 565 nm and 615 nm while a third optical channel operates on a wavelength greater than 630 nm. Other embodiments use two optical channels operating on respective spectral regions. It will be appreciated by those skilled in the art that more or fewer optical channels may be utilized. It is noted that the wavelength of light to be processed by the various optical channels depends upon the wavelength of light produced by the optical source 20 and emitted from the substrate. Those skilled in the art will know to adapt the source and measured wavelengths in accordance with the teachings of the present invention as described below. In one embodiment, the photodetectors, 68, 78 and 88, comprise photomultipliers (PMTs). The photodetectors detect light having wavelengths passed by the respective filters. While the filters are shown in FIG. 1 as being positioned in front of the pinhole elements, the filters can also be positioned between the pinhole elements and the photodetector.

FIG. 1 primarily discloses the generation of a first beam of light and subsequent processing of that first beam of light by mechanical scanning apparatus 40, the substrate 45 and the various optical detection channels. A second beam of light and detection circuit (not shown) is also coupled to the mechanical scanning apparatus 40 and delivered thereby to the substrate 45 in a manner similar to that described above with respect to the first beam of light. The second optical source and detection circuit (not shown) operates in substantially the same manner as described above with respect to the portions of optical scanning system 10 excluding the mechanical scanning system and substrate.

A second optical source (not shown) or, optionally, light diverted from or otherwise provided by the first optical source 30, is provided to the mechanical scanning apparatus 40 via a forward path 33A. The mechanical scanning apparatus 40 directs the second beam of light to the substrate 45 via a second optical path 34A. Light reflected or emitted by the substrate 45 is coupled back to the mechanical scanning apparatus 40 via path 34A and to a second set of one or more optical detection channels (not shown) by a return optical path 35A.

Thus, the optical scanning system discussed above with respect to FIG. 1 produces two light beams which are imparted to a substrate 45 via a mechanical scanning system 40. The resulting fluorescence of the substrate 45 is returned by respective optical paths to respective optical detection channels. The use of two optical scanning systems to scan a substrate results in more rapid scanning of the substrate.

Optical scanning system 10 may also use light reflected from the surface of substrate 45 (or from a selected structure on the surface) for focusing. This is referred to as auto-focusing and is described in U.S. Pat. No. 5,981,956, which is incorporated by reference in its entirety.

Figure 2A:
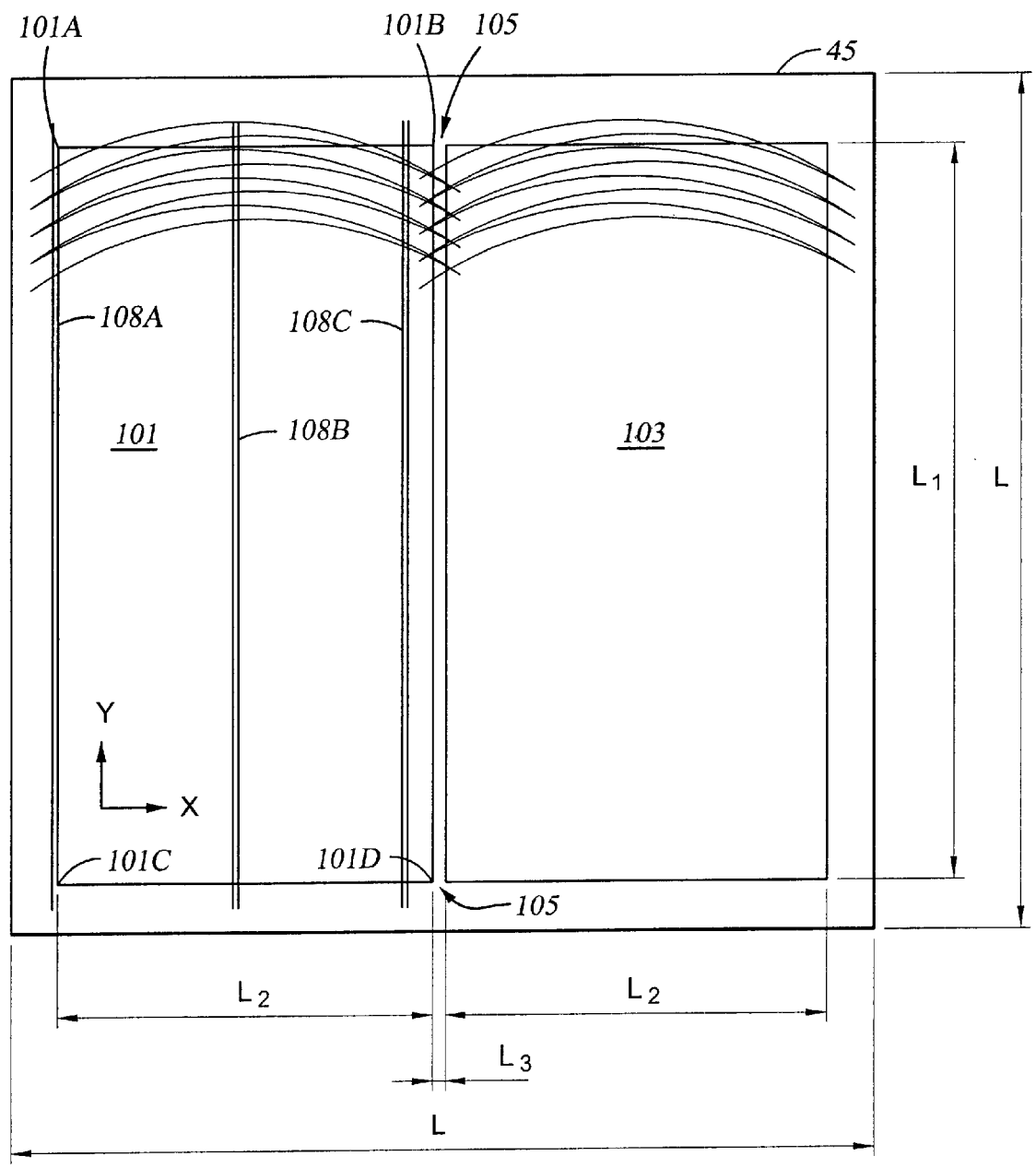
FIGS. 2A and 2B are top views of substrates with several active areas scanned by the scanning modules of FIG. 2.

FIG. 2 depicts an embodiment of an arc scanning system 43. The arc scanning system 43 includes two scanning modules 130A and 130B. Each scanning module is designed for one objective lens that scans substrate 45 via a series of arcuate paths, such as shown in FIG. 2A. Scanning modules 130A and 130B include respective galvanometers (or oscillating motors) 132A and 132B, mounted on respective galvanometer holders 136A and 136B and connected to respective scan arms 140A and 140B by respective galvanometer shafts 138A and 138B, respectively. As used herein, a scan arm is broadly defined as a support for supporting one or more lenses. Each scanning module may also include a position sensor connected to a servo amplifier. Galvanometer holders 136A and 136B may be independently supported on a movable support that allows for focus adjustment. This movable support is constructed to move galvanometer holder 136A or 136B relative to substrate 45 for inspection or imaging of the substrate. The movable support may be motorized and computer controlled by controller 15 (FIG. 1) for imaging different regions of substrate 45 or for focusing relative to the substrate surface. The focusing mechanism can preferably track a non-flat substrate region.

Galvanometers 132A and 132B are constructed to oscillate scan arms 140A and 140B around axes 139A and 139B, respectively. Scan arms 140A and 140B support objective lenses 142A and 142B, and folding mirrors 144A, 144B, 146A, 146B, which move during the oscillation, while mirrors 150A and 150B are stationary. Folding mirrors 146A, 146B, 150A and 150B are located approximately on the axis of rotation of scan arms 140A and 140B. Scan arms 140A and 140B and the associated elements are preferably built with counter-weights 145A and 145B so that the entire assembly, including the galvanometer armature, is balanced.

Folding mirrors 150A and 150B receive light beams over the respective optical paths 33A and 33B and provide the light beams to the respective periscopic structures formed by mirrors 144A, 144B, 146A, and 146B. Objective lenses 142A and 142B provide focused beams 34A and 34B to substrate portions 101 and 103, respectively. Each objective lens has a large numerical aperture, for example, 0.5 and preferably larger than 0.6. Each scanning module may be designed as described in the PCT application US99/06097, published as WO 99/47964, which is incorporated herein by reference in its entirety.

Scan arms 140A and 140B extend from oscillation axes 139A and 139B, respectively, and oscillate approximately +/−30 degrees from the centered position. In this manner, objective lenses 142A and 142B scan over arcs in substrate portions 101 and 103 (FIG. 2A). In general, each scan arm 140 oscillates over an angle that is in the range of approximately +/−10 degrees to +/−50 degrees from a centered position. In the oscillation process, each scan arm 140 examines one substrate portion, which is in the range of about 30 mm to about 70 mm wide (not including overshoot excursion necessary for deceleration and acceleration, i.e., motion reversal). To minimize heating of the motor, the moment of inertia of the scan arms should be as small as possible. In one aspect, the scanning module can scan very large substrates with very small lenses which have high numerical apertures.

The optical system may include one or more translation stages and, optionally, a level stage. The translation stages displace substrate 45 step-by-step or continuously in the Y direction relative to the axes of rotation 139A and 139B and in the X direction to advance the substrate to a new inspection position. The level stage displaces substrate 45 primarily in the Z direction and positions the illuminated surface (i.e., the proximal or distal surface of substrate 45, depending on the type of substrate 45) within the depth of field of lenses 142A and 142B. The level stage is described in detail in U.S. patent application Ser. Nos. 09/079,790 and 09/500,548, both of which are incorporated herein by reference in their respective entireties.

Alternatively, the optical system includes two translation stages. The first translation stage displaces substrate 45 step-by-step or continuously in the Y direction, as described above. The second translation stage, however, is used to support and displace galvanometer holder 136A in the Z direction to adjust the position of lens 142A, and position the illuminated surface within the depth of field. Another translation stage may be used to support and displace galvanometer holder 136B in the Z direction to adjust the position of lens 142B. In addition, a third translation stage is preferably used to advance the substrate in the X direction to a new inspection position.

In one embodiment of an arc scanner, each lens is mounted on a separate scan arm (or other lens support) and each scan arm is coupled to a separate motor. Each of the two scan arms carries an objective lens (and, optionally, a position sensor). The scan arms may be independently supported to allow relative translation, tilting or rocking. During the scanning process, the two scan arms, including the two objective lens, move synchronously like "windshield wipers" while the lenses scan over a pattern shown in FIG. 2A.

Figure 2B:
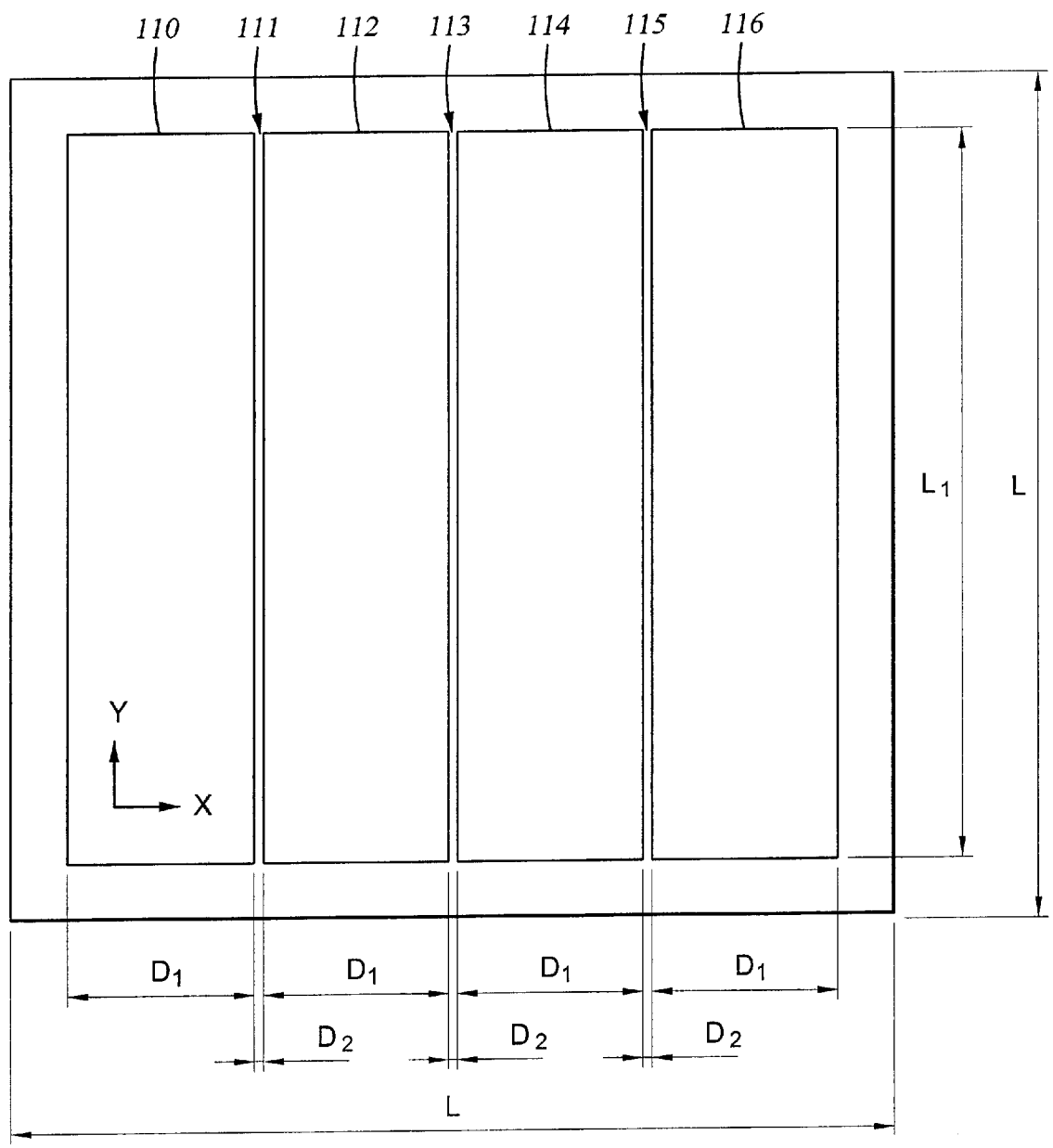

Referring to FIGS. 2A and 2B, substrate 45 may include one or more (four are shown) active areas depending on a selected application. For example, substrate 45 may have an overall area of 125 mm×125 mm with a usable area of 111 mm×111 mm with the edges being used for a sealing o-ring and a mounting bracket of a flow cell. The usable area of the substrate may be divided into two 55 mm wide and 110 mm long synthesis areas 101 and 103, separated by a 1-mm by 110-mm blank lane 105, as shown in FIG. 2A. Alternatively, the usable area of substrate 45 may be divided into four 27 mm wide and 110 mm long synthesis areas 110, 112, 114 and 116, separated by respective 1-mm by 110-mm blank lanes 111, 113, 115, as shown in FIG. 2B. In an embodiment in which two scan arms are used, areas 110 and 114 may be scanned simultaneously by the two scan arms. The substrate can then be indexed in the X axis and areas 112 and 116 can then be scanned simultaneously by the two arms. Those skilled in the art informed by the teachings of the present invention will readily devise substrates and/or active area configurations having different measurements than that described above. The substrates are typically configured to define active areas and blank areas so that two or more active areas can be scanned without requiring that "stitching" of the results from the scanned active areas.

Control features may be disposed on the substrates and spaced evenly a selected distance apart. The control features may be used to ensure proper alignment and/or positioning of a substrate in the system.

For example, substrate 45 may optionally include chromium control features used, for example, for focusing and alignment. Chromium control features may be chromium stripes located, for example, along the Y direction, such as stripes 108A, 108B and 108C, shown in FIG. 2A. The location of control features may be optimized with respect to the location of active areas, substrate size, and the size of the scan arms. Alternatively, other patterns, such as a checker board or bull's eye pattern, can be used for alignment or focusing purposes. The use of the chromium control features is not necessary to practice the invention.

To determine the height of best focus and detect whether substrate 45 is tilted or bowed, two or more positions on the substrate can be detected and analyzed prior to inspection to ensure clarity of focus. This information is stored in computer memory and accessed later during a subsequent fine resolution "examination" scan. With respect to gross height error due to pitch, roll or bow, the computer program analyzes the pre-scan focus data and determines gross tilt correction. The actuators of the level stage are set accordingly to correct gross tilt prior to the examination scan.

During the examination scan, substrate 45 is held on its support in exactly the same position it occupied in the pre-scan. When the examination scan occurs, the focus mechanism continually tracks the surface of substrate 45 in accordance with the stored data. The translation stage can advance substrate 45 step-by-step using a stepper motor. The system controller drives the galvanometer at a constant angular velocity during the data collection part of excursions. Scanned data may be acquired in various ways, for instance, with index motion of the object between scans, performing clockwise rotation only, or with both clockwise and counterclockwise motions, as shown in FIG. 2A. A symmetric triangular waveform can be used to gather data in both directions. A saw tooth waveform can be used to collect data in one direction.

Scanning modules 130A and 130B (as described above) are constructed with scan arms 140A and 140B having a selected length to best achieve the required focus for a given scan width. By maximizing the arm length and the scan width while maintaining required focus, substrates can be scanned faster. One skilled in the art will choose appropriate scan arm lengths given substrate size, synthesis area size and can optimize scan arm length for substrates of varying flatness.

In one embodiment, scanning modules 130A and 130B have scan arms 140A and 140B mounted on separate Cambridge Technology (Cambridge Mass.) model 6880-366 galvanometers. Each galvanometer is driven by a Cambridge Technology model 67088-366 driver board, which contains analog servo electronics and a high-current amplifier. A National Instruments (Austin Tex.) model NI 5411 arbitrary waveform generator generates a symmetric triangular wave with rounded corners. The waveform generator output is provided to the driver board input. A data acquisition duty cycle includes the linear portion of the triangular waveform, which is about 75% to 80% of the total duty cycle. (The data acquisition duty cycle excludes the waveform portion used for acceleration and deceleration.) The waveform generator board contains four digital output channels in addition to its analog output channel. The first digital output is used as a pixel clock for the first galvanometer, the second digital output is used as a pixel clock for the second galvanometer, the third digital output is used as a line clock that indicates the beginning of each forward scan line, and the fourth digital output is used as a line clock that indicates the beginning of each reverse scan line.

The objective lenses 142A and 142B are preferably small aspheric lenses molded from one piece of material. The lenses have a relatively large numerical aperture and a relatively small mass. In one embodiment, the objective lens comprises a lens made by Geltech (model 350230) with a focal length of about 4.5 mm and a numerical aperture, NA=0.55. The lens focused a 488 nm laser beam with a diameter of about 0.93 mm to a spot with a diameter of about 3 microns (wherein the diameters are given at the 1/e-squared intensity points). Another suitable lens is the lens model 350330 (made by Geltech) with a focal length of about 3.1 mm and NA=0.68. This lens focuses a laser beam with a diameter of about 0.64 mm to a spot with a diameter of about 3 microns.

In this system, light detector 68 is a Hamamatsu (Bridgewater N.J.) HCl2O photosensor unit. This photosensor unit includes a Hamamatsu R6357 photomultiplier for detecting the fluorescent radiation. The photomultiplier output is low-pass filtered by a 4-pole Bessel filter and is digitized by a data acquisition board containing a 12-bit A/D converter, made by Computer Boards Inc. (Middleboro Mass.) model CIO-DAS 16/MI. The A/D conversions are triggered by pixel clock pulses generated by the waveform generator board.

This embodiment of scanning system 10 includes at least two 2 photosensor modules, 2 low-pass filters, and 2 data acquisition boards (one for each scan arm 140A and 140B). For simultaneous two or three color fluorescence detection, scanning system 10 includes four or six photosensor modules and low-pass filters, in the arrangement shown in FIG. 1. The CIO-DAS 16/MI data acquisition board includes 8 analog input channels, which can accommodate the six detectors. If the data acquisition speed is inadequate when both data acquisition boards are installed in the same computer, the data acquisition boards can be installed in 2 different computers. For simultaneous two or three color detection, the data acquisition speed may be increased using a PCI-bus board such as the Computer Boards Inc model PCI-DAS4020112 (instead of the CIO-DAS 16/M1 data acquisition board which is an ISA-bus board).

According to one embodiment, the pixel size is 2.27 microns and there are 12,288 pixels per arc. Each scan arm scans at a rate of 9.3 cycles per second, giving a data acquisition rate of 18.6 arcs per second, by taking data in both the forward and reverse (cw and ccw) directions. The peak current in the galvanometer coil is typically about 1 A, and the galvanometer housing reaches a temperature of only about 2 degrees C. above ambient. In general, a large current may raise the temperature unacceptably, which poses a limit to the scan rate. Frequently, the limiting factor for fast scanning is not due to limitations of the scanner, but is limited by the amount of light collected from each fluorophore, i.e., the quality of the data collected. Thus, to obtain a sufficiently high signal to noise ratio, the scan speed may have to be reduced. For target molecules labeled with biotin and stained with streptavidin/phycoerythrin, for example, scanning at a rate of 18.6 lines per second provides adequate signal to noise ratio. The system scans 110 mm×110 mm substrate in 1.5 hours with scan arms 140A and 140B (compared to about 3 hours with only one scan arm using one flying objective lens). The amount of data acquired per substrate is about 2.25 gigapixels (4.5 gigabytes) per color.

Referring to FIG. 3, according to another embodiment, scanning system 40 includes an arc scanning system 43A with three rotational scanning modules. Rotational scanning modules 130A, 130B and 130C are designed to displace three objective lenses over arcuate paths, similar to the two-arm embodiment described in the embodiment of FIG. 2. The components are similar to those described above with the inclusion of a third arm.

Figure 3A:
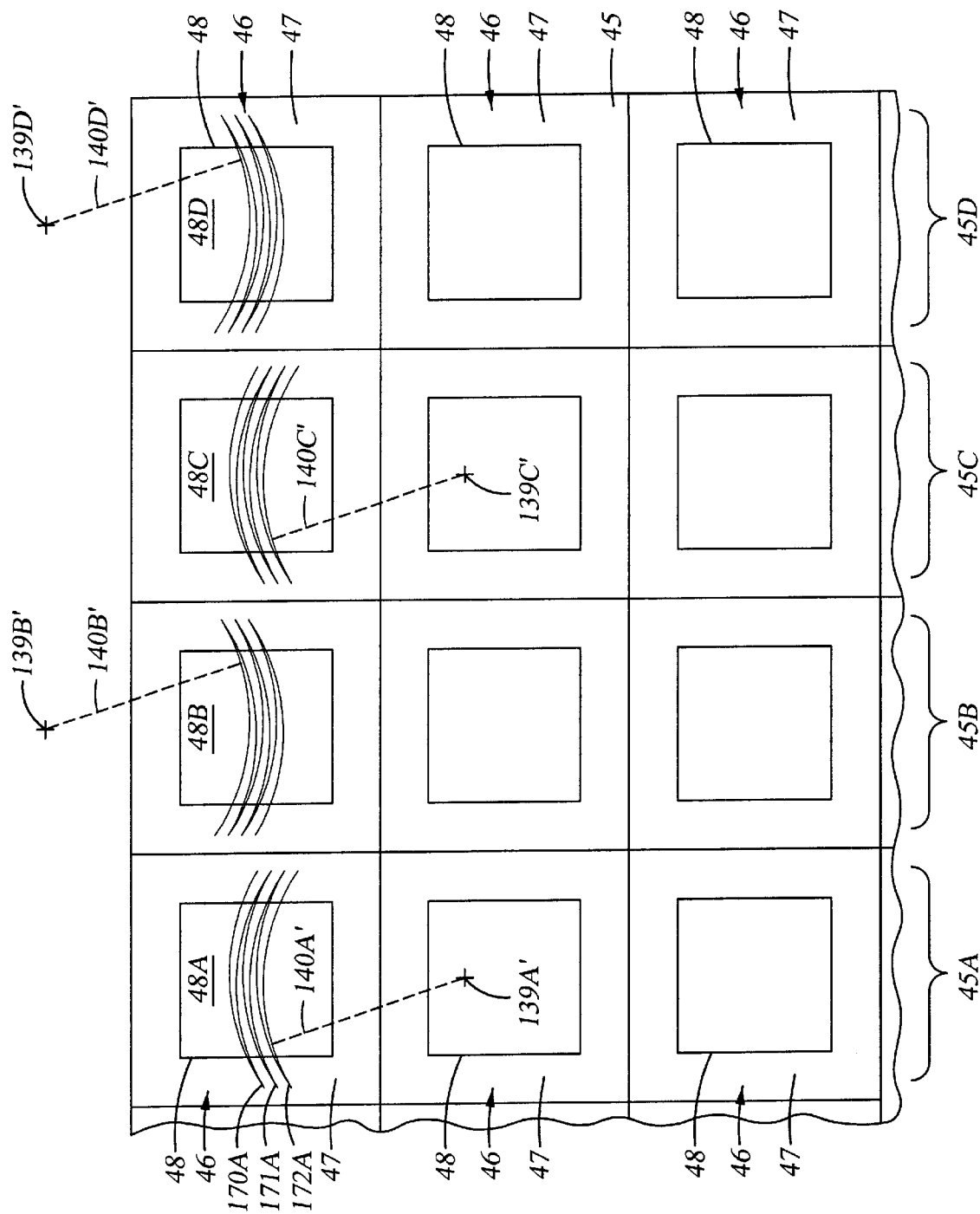
FIG. 3A illustrates substrate scanning patterns for a different arrangement of scanning modules.

FIG. 3A illustrates an example of a substrate with several active areas and also illustrates a scanning pattern for four rotational scanning modules. The illustrated portion of substrate 45 includes several active areas 45A, 45B, 45C, 45D, for example, several microarrays 46 (such as microarrays made by Affymetrix, Inc., located in Santa Clara, Calif.) distributed over the substrate surface. Each microarray 46 has an overall area (optionally delineated by lines 47) and an active area (delineated by a square formed by lines 48). Substrate 45 may be about 12,100 mm² (110 mm×110 mm) with 49 microarrays, each having the active area of 12.8 mm×12.8 mm and a 3 mm blank lane, forming together the area of 15.8 mm×15.8 mm. The blank lanes may be used to divide substrate 45 into separate compartments for hybridization. In general, lines 47 are optional metallic lines used for alignment or focusing before or during the scan, or used for reference during data analysis.

Still referring to FIG. 3A, and according to yet another embodiment, the optical scanning system includes four rotational scanning modules similar to modules 130A, 130B shown in FIG. 2. The four rotational scanning modules include four scan arms shown schematically by dashed lines 140A', 140B', 140C', and 140D'constructed to oscillate about axes 139A', 139B', 139C and 139D', respectively. The scan arms are disposed in an arrangement in which the direction of the extension of the arms from their axis of rotation alternates in an opposing manner. This geometrical arrangement can accommodate rotational scanning modules with relatively large galvanometers and galvanometer holders that could not be arranged next to each other. Each scan arm supports one objective lens arranged for scanning one active region. For example, scan arm 140A scans active region 48A, as shown by lines 170A, 171A, 172A.

Referring to FIG. 4, scanning module 42 includes a scan arm (armature) 201, which carries objective lenses 220 and 220A and folding mirrors 222, 224 and 224A, forming thereby a "double periscope." The entire structure has a very low mass. Double-sided mirror 222, mounted at 45 degrees with respect to axis A, provides light paths 226 and 226A, which lie on the long axis of the rotating scan arm and are directed to lens-illuminating mirrors 224 and 224A. Lens-illuminating mirrors 224 and 224A, located also on-axis with objective lenses 220 and 220A (i.e., on axes A' and A", which preferably are substantially parallel with axis A) provide light paths 228 and 228A, respectively. Preferably, the length of the light paths to lenses 220 and 220A is constant throughout the scanning range. This enables the use of simple alignment techniques.

Scan arm 201 has a symmetrical construction with the corresponding optical elements having approximately the same masses and symmetrical locations of objective lenses 220 and 220A and mirrors 224 and 224A with respect to the Z axis of rotation. According to another embodiment, armature 201 may have a nonsymmetrical construction, wherein mirrors 224 and 224A are located at different distances with respect to the Z-axis of rotation. In this embodiment, scan arm 201 also includes at least one counter weight selected to achieve a counterbalanced condition, or the system may employ another balancing technique. In both embodiments, light paths 35 and 35A are coupled into the scan arm along axis A. Light path 35 is coupled into scan arm using mirrors 218 and 222, and light path 35A is coupled into scan arm using mirrors 219 and 222.

The present apparatuses and methods may find application in the field of gene sequencing, the field of histology (for studying histochemical stained and immunological fluorescent stained images), or fluorescence in situ hybridization. The present apparatuses can image an array of probe sequences fabricated on a substrate. According to one embodiment, the target molecules are labeled with biotin, which is not a dye, but facilitates labeling. The substrate or the active areas separately are hybridized. After hybridization and washing, the substrate is stained with streptavidin-phycoerythrin. Streptavidin binds very strongly to biotin. Phycoerythrin (which is covalently attached to the streptavidin) is a very brightly fluorescent dye with absorption maxima at 480–565 nm and an emission maximum at 578 nm.

If a multi-labeling scheme is utilized, a wavelength which approximates the mean of the various candidate labels' absorption maxima may be used. Alternatively, multiple excitations may be performed, each using a wavelength corresponding to the absorption maximum of a specific label. Various types of fluorophores (and their corresponding absorption maxima) are Fluorescein (488 nm), Dichloro-fluorescein (525 nm), Hexachloro-fluorescein (529 nm), Tetramethylrhodamine (550 nm), Rhodamine X (575 nm), Cy3™ (550 nm), Cy5™ (650 nm), Cy7™ (750 nm), and IRD4O (785 nm).

The present apparatuses and methods may find application in the field of gene sequencing, the field of histology (for studying histochemical stained and immunological fluorescent stained images), or fluorescence in situ hybridization. The present apparatuses can image an array of probe sequences fabricated on a substrate.

Thus, the present invention provides in one aspect an optical scanner having at least a first and a second objective lens mounted on at least one scanning module, wherein each at least one scanning module comprises at least one motor, at least one scan arm and at least one of the objective lenses; an optical coupling system comprising a light source and at least a first and second detector, wherein said optical coupling system is configured to deliver light from said light source through said at least two objective lenses to a substrate and detect light from said substrate collected by said at least a first and a second objective lens, and wherein said first detector detects light from said first objective lens and said second detector detects light from said second objective lens and so on; and a translation mechanism constructed for relative movement of said substrate and said scanning module. The translation mechanism may include a translation table arranged to receive said substrate and configured to displace linearly said substrate with respect to said scanning module. Also, the optical coupling system may further comprise a single laser beam and a beam splitter. Furthermore, the optical coupling system may further comprise at least one additional element selected from the group of mirror or prism element, light filter element, and pinhole element. In addition, the motor of the present invention may be a galvanometer or a servomotor. In addition, in one embodiment of the present invention, each objective lens is a single aspheric lens, and may have a numerical aperture of at least about 0.5. Also, it is preferred that the scanning modules have a moment of inertia less than 3000 gxcm$^2$, or even less than about 300 gxcm$^2$. In an alternative embodiment, the light source may comprise at least two lasers and said optical coupling system delivers a light beam from a different laser to a different objective lens. In another embodiment of this aspect of the invention, the coupling system is configured to detect fluorescent radiation emitted from said substrate in response to said delivery of light from said light source.

In another aspect of the present invention, there is provided an optical scanner, comprising: a first and a second scanning module, wherein each of said scanning modules comprises a motor, a scan arm and an objective lens; an optical coupling system comprising a light source and a first and a second detector, wherein said optical coupling system is configured to deliver light from said light source through said first and second objective lenses to a substrate and detect light from said substrate collected by said first and second objective lenses, and wherein said first detector detects light from said first objective lens and said second detector detects light from said second objective lens; and a translation mechanism constructed for relative movement of said substrate and said scanning module. In this aspect of the invention, the translation mechanism may include a translation table arranged to receive said substrate and configured to displace linearly said substrate with respect to said scanning module. Also, the optical coupling system may further comprise a single laser beam and a beam splitter. Furthermore, the optical coupling system may further comprise at least one additional element selected from the group of mirror or prism element, light filter element, and pinhole element. In addition, the motor of the present invention may be a galvanometer or a servomotor. In addition, in one embodiment of the present invention, each objective lens is a single aspheric lens, and may have a numerical aperture of at least about 0.5. Also, it is preferred that the scanning modules have a moment of inertia less than 3000 gxcm$^2$, or even less than about 300 gxcm$^2$. In an alternative embodiment, the light source may comprise at least two lasers and said optical coupling system delivers a light beam from a different laser to a different objective lens. In another embodiment of this aspect of the invention, the coupling system is configured to detect fluorescent radiation emitted from said substrate in response to said delivery of light from said light source.

In an alternative aspect of the present invention, there is provided an optical scanning method for examining biological material, comprising the acts of: providing two objective lenses mounted on at least one scanning module, wherein each of said at least one scanning module comprises at least one motor, at least one scan arm and at least one of the at least one objective lenses; generating light of a selected wavelength and coupling said generated light to said two objective lenses; displacing said at least one scanning module on a scan path over biological material disposed on regions of a substrate; irradiating said biological material by light from each objective lens; collecting light from said biological material by each objective lens; detecting by a separate detector light collected from each objective lens; and analyzing said biological material based on said light detected by said detectors. In one embodiment of this aspect, the objective lenses are mounted on separate scanning modules. In another embodiment, each of said objective lenses is a single aspheric lens, with a numerical aperture of at least about 0.5. Further, each of said at least two scanning modules has a moment of inertia less than 3000 gmxcm$^2$, or even less than about 300 gmxcm$^2$. Further, one embodiment provides a scan path is arcuate with respect to said substrate.

The optical scanning system may include a dynamic focusing system constructed to displace the large area substrate during the periodic scan. Each of the two modules may include a dynamic focusing system. The dynamic focusing system may be constructed to displace the large area substrate to achieve a depth of focus of less than about 10 $\mu$m. The focusing system may include a tilt focusing mechanism. The focusing system may be constructed to displace, prior to performing the periodic scan, the large area substrate to achieve a depth of focus of less than about 10 $\mu$m.

A single substrate or several substrates with the active subareas may be coupled to a translator (e.g., a translation table for moving the substrate, or a rail for moving the support structure) constructed and arranged to move the substrate or the support structure with respect to each other. The drivers and the translator are cooperatively arranged for the first and second objective lenses to scan completely the first and second active areas, respectively. The first and second active areas are offset from each other by a distance in a direction that is substantially orthogonal to the translation direction. Alternatively, the first and second active areas are offset from each other by a distance in a direction that is substantially parallel to the translation direction.

While the foregoing is directed to embodiments of the present invention, other and further embodiments of the invention may be devised without departing from the basic scope thereof, and the scope thereof is determined by the claims that follow.

What is claimed is:

1. An optical scanner, comprising:
   at least a first and a second objective lens mounted on at least one scanning module, wherein each at least one scanning module comprises at least one motor, at least one scan arm and at least one of the objective lenses;
   an optical coupling system comprising a light source and at least a first and second detector, wherein said optical coupling system is configured to deliver light from said light source through said at least two objective lenses to a substrate and detect light from said substrate collected by said at least a first and a second objective lens, and wherein said first detector detects light from said first objective lens and said second detector detects light from said second objective lens and so on; and a translation mechanism constructed for relative movement of said substrate and said scanning module.

2. The optical scanner of claim 1, wherein said translation mechanism includes a translation table arranged to receive said substrate and configured to displace linearly said substrate with respect to said scanning module.

3. The optical scanner of claim 1, wherein said optical coupling system further comprises a single laser beam and a beam splitter.

4. The optical scanner of claim 1, wherein said optical coupling system further comprises at least one additional element selected from the group of mirror or prism element, light filter element, and pinhole element.

5. The optical scanner of claim 1, wherein said motor is a galvanometer or a servomotor.

6. The optical scanner of claim 1 wherein each objective lens is a single aspheric lens.

7. The optical scanner of claim 1 wherein each objective lens has a numerical aperture of at least about 0.5.

8. The optical scanner of claim 1 wherein each scanning module has a moment of inertia less than 3000 g×cm$^2$.

9. The optical scanner of claim 8 wherein each scanning module has a moment of inertia of less than about 300 g×cm$^2$.

10. The optical scanner of claim 1 wherein said light source comprises at least two lasers and said optical coupling system delivers a light beam from a different laser to a different objective lens.

11. The optical scanner of claim 10 wherein each of said at least two lasers emits a different, single wavelength light.

12. The optical scanner of claim 1 wherein said optical coupling system is configured to detect fluorescent radiation emitted from said substrate in response to said delivery of light from said light source.

13. An optical scanner, comprising:
a first and a second scanning module, wherein each of said scanning modules comprises a motor, a scan arm and an objective lens;
an optical coupling system comprising a light source and a first and a second detector, wherein said optical coupling system is configured to deliver light from said light source through said first and second objective lenses to a substrate and detect light from said substrate collected by said first and second objective lenses, and wherein said first detector detects light from said first objective lens and said second detector detects light from said second objective lens; and
a translation mechanism constructed for relative movement of said substrate and said scanning module.

14. The optical scanner of claim 13, wherein said translation mechanism includes a translation table arranged to receive said substrate and configured to displace linearly said substrate with respect to said scanning module.

15. The optical scanner of claim 13, wherein said optical coupling system comprises a single laser beam and a beam splitter.

16. The optical scanner of claim 13, wherein said optical coupling system further comprises at least one additional element selected from the group of mirror or prism element, light filter element, and pinhole element.

17. The optical scanner of claim 13, wherein said motor is a galvanometer or a servomotor.

18. The optical scanner of claim 13, wherein each of said objective lenses is a single aspheric lens.

19. The optical scanner of claim 13, wherein each of said objective lenses has a numerical aperture of at least about 0.5.

20. The optical scanner of claim 13, wherein each of said two scanning modules has a moment of inertia less than 3000 g×cm$^2$.

21. The optical scanner of claim 13, wherein each of said two scanning modules has a moment of inertia of less than about 300 g×cm$^2$.

22. The optical scanner of claim 13, wherein said light source comprises a first and a second laser and said optical coupling system delivers a light beam from said first laser to said first objective lens and a light beam from said second laser to said second objective lens.

23. The optical scanner of claim 22, wherein said first and said second lasers emit a different, single wavelength light.

24. The optical scanner of claim 13 wherein said optical coupling system is configured to detect fluorescent radiation emitted from said substrate in response to said delivery of light from said light source.

25. The optical scanner of claim 13 wherein said two scanner modules are configured to perform scans over separate, non-overlapping scan paths.

26. The optical scanner of claim 25 wherein said scanning modules are configured to move over arcuate scan paths with respect to said substrate.

27. The optical scanner of claim 26 wherein said scanner modules are configured to move said two objective lenses in a synchronized scan motion.

28. The optical scanner of claim 13, wherein said scanner modules are constructed to move over arcuate scan paths with respect to said substrate, and wherein said arcuate scan path of said first scanner module is oriented 180 degrees with respect to said arcuate scan path of said second scanner module.

29. The optical scanner of claim 13, wherein said scanner modules are constructed to move over arcuate scan paths with respect to said substrate, and wherein said arcuate scan path of said first scanner module is oriented 0 degrees with respect to said arcuate scan path of said second scanner module.

30. An optical scanning method for examining biological material, comprising the acts of:
providing two objective lenses mounted on at least one scanning module, wherein each of said at least one scanning module comprises at least one motor, at least one scan arm and at least one of the at least one objective lenses;
generating light of a selected wavelength and coupling said generated light to said two objective lenses;
displacing said at least one scanning module on a scan path over biological material disposed on regions of a substrate;
irradiating said biological material by light from each objective lens;
collecting light from said biological material by each objective lens;
detecting by a separate detector light collected from each objective lens; and
analyzing said biological material based on said light detected by said detectors.

31. The optical scanning method of claim 30, wherein said objective lenses are mounted on separate scanning modules.

32. The optical scanning method of claim 30, wherein each of said objective lenses is a single aspheric lens.

33. The optical scanning method of claim 30, wherein each objective lens has a numerical aperture of at least about 0.5.

34. The optical scanning method of claim 30, wherein each of said at least two scanning modules has a moment of inertia less than 3000 gm×cm$^2$.

35. The optical scanning method of claim 30, wherein each of said at least two scanning modules has a moment of inertia less than about 300 gm×cm².

36. The optical scanning method of claim 30, wherein said scan path is arcuate with respect to said substrate.

37. The optical scanning method of claim 30, wherein said objective lenses are mounted on separate scanning modules and wherein said scan paths of each scanning module is arcuate with respect to said substrate.

38. The optical scanning method of claim 37, wherein said scanning modules move synchronously with respect to each other.

* * * * *